United States Patent [19]

Schuman et al.

[11] 4,029,661

[45] June 14, 1977

[54] PROCESS FOR PRODUCING 5-FLUOROURACIL AND DERIVATIVES THEREOF IN ACID AND/OR ALCOHOL SOLVENTS

[75] Inventors: Paul D. Schuman, Hawthorne; Geraldine Westmoreland; Roy Anderson, both of Gainesville, all of Fla.

[73] Assignee: PCR, Inc., Gainesville, Fla.

[22] Filed: July 13, 1972

[21] Appl. No.: 271,489

Related U.S. Application Data

[63] Continuation-in-part of Ser. No. 186,443, Oct. 4, 1971.

[52] U.S. Cl. .......................... 260/256.4 C; 260/260
[51] Int. Cl.² ........................................ C07D 239/54
[58] Field of Search ................... 260/260, 256.4 C

[56] References Cited

UNITED STATES PATENTS

| | | | |
|---|---|---|---|
| 3,682,917 | 8/1972 | Knuniants | 260/260 |
| 3,846,429 | 11/1974 | Giller et al. | 260/260 |

*Primary Examiner*—Paul M. Coughlan, Jr.
*Attorney, Agent, or Firm*—Murray and Whisenhunt

[57] ABSTRACT

Direct fluorination of uracil, cytosine and their derivatives, in the presence of a non-aqueous solvent, by fluorine gas to produce 5-fluorouracil, 5-fluorocytosine, 5-fluorouracil derivatives and 5-fluorocytosine derivatives is disclosed. The non-aqueous solvent is an acid or alcohol, which can be partly or fully fluorinated or chlorinated, of up to 8 carbon atoms, such as trifluoroacetic acid. Novel compounds produced by the reaction, such as 5,5-difluoro-5,6-dihydro-6-(2,2,2-trifluoroethoxy) uracil are also disclosed. The derivatives and 5-fluorocytosine are useful as germicidal and antineoplastic agents while 5-fluorouracil itself is a known cancer chemotherapy agent.

24 Claims, No Drawings

PROCESS FOR PRODUCING 5-FLUOROURACIL AND DERIVATIVES THEREOF IN ACID AND/OR ALCOHOL SOLVENTS

CROSS-REFERENCE TO RELATED APPLICATION

This application is a continuation-in-part of our co-pending application Ser. No. 186,443, filed Oct. 4, 1971.

BACKGROUND OF THE INVENTION

The present invention relates to a novel process for preparing uracil and cytosine derivatives and novel chemical compounds so produced.

Uracil has been reacted with various compounds to achieve substitution in the 5 position, see "Chlorination of 2,4-Diketotetrahydropyrimidines by Action of a Mixture of Superoxol and Hydrochloric Acid", Jour. Am. Chem. Soc., Vol. 65, pt. 1, pp. 1218–1219 (1943); "Action of Alkali and Ammonia on 2,4-Dialkoxypyrimidines", Jour. Am. Chem. Soc., Vol. 56, pt. 1, pp. 134–139 (1934); "The Reaction of Bromine with Uracils", Jour. Org. Chem., Vol. 24, p. 11, Jan., 1959; Wang, "Reaction of Bromine with Uracils", Nature 180, pp. 91–92 (July 13, 1957), and Brown infra.

The reaction of bromine or chlorine with uracil is as follows:

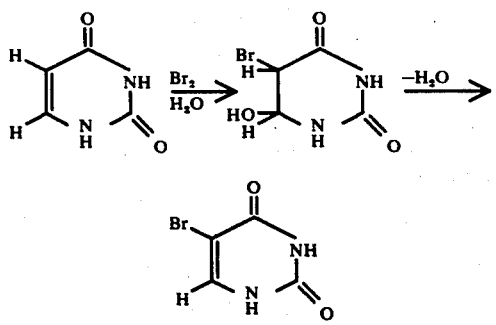

Numerous references may be cited which demonstrate the extreme reactivity of fluorine in contrast to the other halogens. For example, see M. Hudlicky, "Chemistry of Organic Fluorine Compounds", The MacMillan Co., New York (1962), and J. H. Simons, "Fluorine Chemistry", Vol. 1, Academic Press, Inc., New York, New York (1950). This extreme reactivity and the presumed required intermediacy of a hypohalous acid addition to the double bond would preclude the predictability of the reaction product of the aqueous fluorination of uracil.

The reaction of elemental fluorine with organic compounds has been studied extensively since the discovery of the gas by Henri Moissan in 1886. Moissan found that unlike chlorine, bromine and iodine, the unmoderated reaction of fluorine with organic compounds results in ignition and ultimate decomposition of the organic compound to smaller molecules. This greatly increased reactivity of fluorine compared to the other halogens is readily explained by comparing the heats of reaction of the halogens as in the following reactions. See M. Hudlicky, "Chemistry of Organic Fluorine Compounds", p. 72, The MacMillan Co., New York (1962).

|  | | $\Delta H°$ (K cal/mole) | | |
|---|---|---|---|---|
| $X =$ | F | Cl | Br | I |
| $C{=}C + X_2 \rightarrow CX{-}CX$ | −107.2 | −33.1 | −18.8 | + 1.2 |
| $C{-}H + X_2 \rightarrow C{-}X + HX$ | −102.5 | −22.9 | − 6.2 | +13.7 |

Since the carbon-carbon bond energy is only about 60 K cal/mole, it is quite evident that unless the heat of reaction is removed rapidly the heat evolved in fluorination is more than sufficient to destroy the carbon skeleton.

A number of methods have been used in which the heat of reaction is dissipated rapidly enough to give fair yields of fluorinated product. The more common methods are: (1) bubbling a mixture of fluorine and an inert gas through a cold liquid; (2) conducting away the heat of reaction by conducting the reaction in the presence of metal packing; and (3) addition of very large amounts of an inert diluent gas. See M. Stacey, J. C. Talow, and A. G. Sharpe, "Advances in Fluorine Chem.", Vol. 2, pp. 196–208, Butterworth, Inc., Washington, D.C. (1961); M. Hudlicky, "Chemistry of Organic Fluorine Compounds", The MacMillan Co., New York (1962); and J. H. Simons, "Fluorine Chemistry", Vol. 1, Academic Press, Inc., New York, N.Y,. (1950).

An aqueous medium has seldom been used to assist in fluorination of organic compounds. Reference may be made to the work of Banks, Haszeldine and Lalu, Chem. and Ind. (London), 1803 (1964), CA 62, 428 g. (1965), in which esters of carbamic acid were fluorinated.

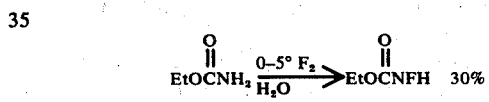

Since uracil exists predominantly in the oxo or keto form, see D. J. Brown, "The Pyrimidines", p. 9, Interscience Publishers, Inc., New York (1962), the results of Bank's work would lead one to belive that fluorination of uracil would result in N fluorination rather than C fluorination, i.e., would yield products containing N-F groups.

It is also known to prepare 5-fluorouracil by reacting uracil mixed with a diluent amount of acetic acid, anhydrous hydrofluoric acid or sulfuric acid and treating the mixture with fluorine mixed with nitrogen as an inert gas at a temperature of 20° to 25° C, see Belgian Pat. No. 748,468 to Knuniants et al. However the yield of 5-fluorouracil produced by this process is generally low and the presence of certain diluents, such as acetic acid, in the reaction mixture tends to give rise to undesirable secondary reaction products.

As previously stated, the process of the present invention is useful for the fluorination of uracil to form 5-fluorouracil, as well as 5-fluorocytosine and novel uracil and cytosine derivatives. The use of 5-fluorouracil in the treatment of cancer particularly dermatological cancers, is known and well documented. See Heidelberger et al, "Studies on Fluorinated Pyrimidines II - Effects on Transplanted Tumors", Cancer Research, Vol. 18, p. 305 (1958), and Heidelberger et al, "Fluorinated Pyrimidines, A New Class of Tumor-Inhibitory Compounds", Nature, Vol. 179, p. 663 March 30, 1957. Bardos et al, Nature 183, 612 (1959), and Brown, D. J. "The Pyrimidines", p. 175, Interscience, New York (1962).

The commercially employed method for the synthesis of 5-fluorouracil disclosed in U.S. Pat. 2,802,005 utilizes extremely toxic monofluoro intermediates. See Stacy et al, "Advances in Fluorine Chemistry", Vol. 2, pp. 196–208, Butterworth, Washington, D.C. (1961). Large scale production has not been undertaken primarily because of the difficulty in handling these intermediates.

It is also known to prepare various uracil derivatives by reacting 5-fluorouracil with chlorine or bromine in the presence of water, as disclosed in Duschinsky et al U.S. Pat. No. 3,277,092. The reaction may be described by the following scheme:

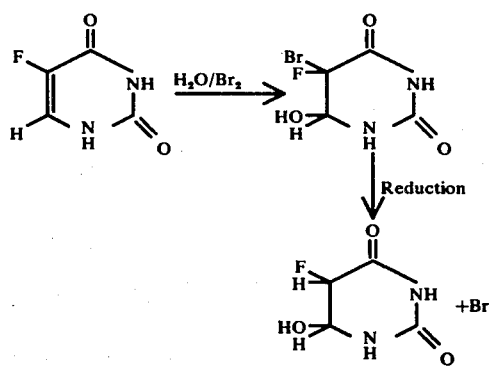

This procedure requires a separate reduction step to remove the bromine, or chlorine, as the case may be, to produce the uracil derivative, in this case 5-fluoro-6-hydroxy-5,6-dihydrouracil.

The direct synthesis of 5-fluorocytosine by the reaction of cystosine with trifluoromethyl hypofluorite is disclosed by Robins et al, "A Direct Synthesis of 5-Fluorocytosine and Its Nucleosides Using Trifluoromethyl Hypofluorite", J.C.S. Chem. Comm. 19, 1972. A similar process is used to produce nucleosides of 5-fluorocytosine.

Uses for 5-fluorocytosine are disclosed in U. S. Pat. Nos. 3,368,938 and 2,945,038, the disclosures of which are hereby incorporated by reference.

DETAILED DESCRIPTION OF THE INVENTION

We have found that uracil, cytosine and derivatives thereof can be reacted directly with fluorine in a reactive non-aqueous medium to produce exceptionally high yields of fluorinated compounds including 5-fluorouracil and 5-fluorocytosine.

According to the disclosed process, the fluorination of uracil and derivatives thereof is accomplished by reacting in an acid or alcohol solvent, as hereinafter described, at a temperature of about 0° C to about the solvent boiling point, a uracil derivative of the formula:

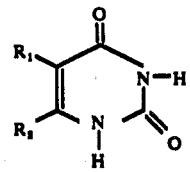

with gaseous fluorine to prepare a compound of the formula

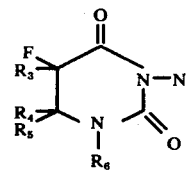

where $R_1$ is hydrogen, fluorine, chlorine, bromine or lower alkyl, $R_2$ is hydrogen or lower alkyl, $R_3$ is hydrogen, fluorine, chlorine, bromine, lower alkyl, or taken with $R_5$, a 5,6-double bond, $R_4$ is hydrogen or lower alkyl, and $R_5$ is a lower alkoxy, including lower haloalkoxy, preferably a lower fluoroalkoxy, a lower acyloxy, including lower haloacyloxy, preferably a lower fluoroacyloxy, a 5,6-double bond when taken with $R_3$, or a 1,6-double bond when taken with $R_6$, and $R_6$ is hydrogen or a 1,6-double bond when taken with $R_5$.

Broadly, the process of the present invention involves the fluorination of uracil, cytosine and derivatives thereof in an acid or alcohol solvent, as hereinafter described, at a temperature from about the solvent freezing point to about the solvent boiling point. Thus, a pyrimidine of the formula

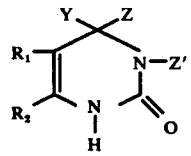

is reacted with gaseous fluorine to produce a compound of the formula

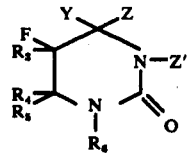

wherein $R_1$, $R_2$, $R_3$, $R_4$, $R_5$ and $R_6$ have the meanings described above, Y is —$NH_2$ and Z and Z' together are a 3,4-double bond or else Y and Z are = O and Z' is hydrogen.

As the reaction medium there may be used a solvent selected from the group consisting of:

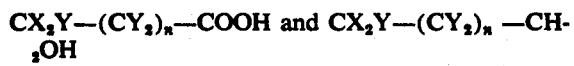

where each X and each Y are independently hydrogen, chlorine or fluorine and $n$ is an integer from 0 to 6. X and Y may also be bromine, but brominated alcohols and acids of the above formulae are not commercially available, so for this reason these products are decidedly not preferred. Illustrative, but not-limiting examples of suitable solvents include the alcohols such as ethanol, propanol, butanol, pentanol, hexanol and the position isomers thereof. Preferably at least some of the hydrogen atoms are replaced by fluorine, chlorine, or bromine atoms such as trifluoro ethanol, heptafluoro butanol, trifluoro butanol and the like; for instance when straight-chain alcohols are used they are at least partially halogenated, most preferably fluorinated. As the acid reaction solvent there may be used, propionic, n-butyric, isobutyric, n-valeric, isovaleric, methylethylacetic, trimethylacetic, caproic, heptoic and caprylic acids and derivatives thereof wherein one or more hydrogen atoms are replaced by bromine, chlorine or fluorine. The preferred acid reaction solvents include trichloroacetic acid, trifluoropropionic acid and trifluoroacetic acid. It is believed that trifluoroacetic acid may be formed in situ from acetic acid, but this is decidedly not preferred. Completely fluorinated acids are preferred over the hydrocarbon acids in general, as the hydrocarbon acids have been found to be somewhat less attractive owing to highly toxic monofluorinated acids that may be present in the reaction mixture and very slow reaction rates, as will hereinafter be described. The above general formulas are presented as an atomic rather than configurational display of suitable solvents, as it will be appreciated that both the alcohols and acids used may be straight chained or branched. Although it is contemplated that higher chain length alcohols may be used, these are at present difficult to obtain commercially, hence the above description. As the halogen substituent there may be mentioned chlorine, bromine and fluorine. Lower alkyl generally designates an alkyl group having from 1 to 6 carbon atoms such as methyl, ethyl, propyl, butyl, hexyl, etc., and the position isomers thereof, including halogen substituted lower alkyl groups such as chloroethyl, bromopropyl, trifluoro methyl, etc. Mixture of solvents may be used if desired.

The reaction may be conducted over a wide range of temperatures. The acid and/or alcohol solvents employed in this process, as hereinabove described, are applied at temperatures not exceeding the boiling point or below the freezing point of the particular solvent or solvents used, and the reaction temperature is usually maintained within the range of about 0° C. to about the boiling point of the solvent. Depending on the particular solvent selected, when the reaction is conducted in an alcohol solvent represented by formula I the preferred range is from 52°-75° C. while when the acids of formula II are used as the reaction solvent the temperature is preferably maintained at about 14 to about 58° C, although when trifluoroacetic acid is used the temperature is preferably about 0° C. The reaction is preferably conducted at atmospheric pressure. Although higher or lower pressures may be used, they involve no particular advantage. Fluorine is preferably introduced into the reaction mixture in admixture with an inert gaseous medium such as nitrogen. The ratio of fluorine to nitrogen or other inert gas is preferably within the range of about 1:1 to about 3:1.

As will be obvious from a consideration of the foregoing suggested reaction scheme there is present at least one mole of gaseous fluorine per mole of uracil, cytosine, or derivative thereof. In practice a molar ratio greater than 1:1 is used to assure completion of the reaction, thus a ratio in excess of 1:1, perhaps even a ratio of fluorine to uracil, cytosine or derivative of 2:1 is employed. While greater amounts of fluorine may be used, there is no particular advantage in doing so and greater costs will be incurred. For convenience of determining the completion of fluorination, the reaction may be stopped when fluorine is detected in the reaction gas effluent or shortly thereafter.

The fluorine gas is preferably bubbled through the solution of uracil, or other pyrimidine, and may be diluted with an inert gas so that is comprises about 10–80, preferably about 50% by volume of the gas mixture. No evidence has been found which would indicate the presence in the reaction mixture of any compounds containing N-F groups in other than trace amounts.

It is of interest to note that fluorination of uracil and uracil derivatives in trifluoro or trichloroacetic acid at elevated temperatures results in a product having a 1–6 double bond. The reaction scheme is as follows:

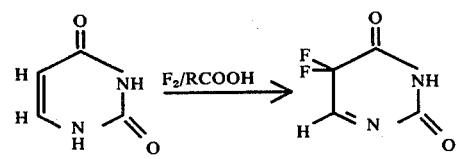

At lower temperatures, generally from 0° to 25° C, preferably about 0°–2° C, novel intermediate compounds are formed in the fluorination of uracil in trifluoroacetic acid. The reaction should be conducted in an inert system, such as in a Teflon-lined system in order for the intermediate products to be isolated. The identification of these novel intermediates has been confirmed by NMR analyses of solutions of such compounds. The solid intermediate compounds have been isolated, but the NMR results have been inconclusive for such isolated compounds. However, infrared analysis indicates that the solid, isolated intermediate compound is not 5-fluorouracil, and heating the intermediate product produces 5-fluorouracil, with evolution of trifluoro acetic acid and hydrofluoric acid, which is consistent with the NMR results for the solutions mentioned above. The structures of the intermediate compounds are as follows:

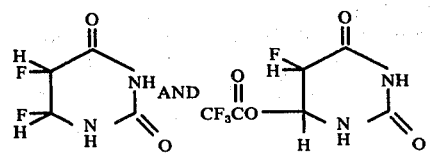

Both of the above intermediate compounds are formed in the reaction mixture produced by fluorinating uracil with gaseous fluorine in trifluoroacetic acid, with the intermediates being formed in approximately a 2:1 ratio of the difluoride to the acetoxy intermediate, depending upon the particular reaction conditions. The reaction mechanism is believed to be as set forth below, but it is to be understood that the present invention is not limited to any particular theory of reaction mechanism, which is presented only as one possible mechanism consistent with the analytical results obtained to date.

Surprisingly, it has been found that the fluorination reaction involves reaction between the fluorine and the reaction solvent, apparently to produce an intermediate product. For instance, when using acid solvent described hereinabove, an acylhypofluoride apparently is formed, such acylhypofluoride probably being of the formula $CX_2Y-(CY_2)_n-COOF$ A corresponding reaction appears to occur when the fluorination is in an alcohol solvent.

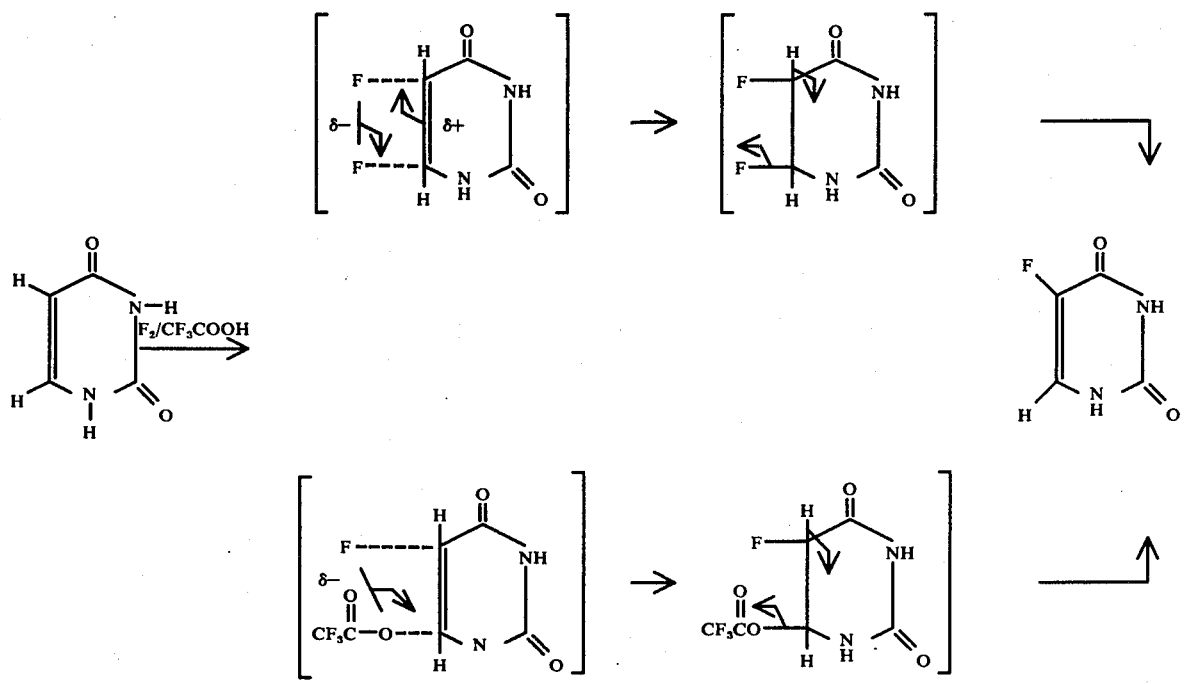

The intermediate compounds allow novel 5-fluoro-6-substituted uracil derivatives to be produced, some of which derivatives cannot be produced by any other known method. The process of producing these novel 6-substituted derivatives is disclosed in the copending application of Schuman and Anderson entitled "6-Substituted-5-Fluoro-Pyrimidine Derivatives" filed on even date herewith Ser. No. 271,490, U.S. Pat. No. 3,954,759, the disclosure of which is hereby incorporated by reference.

In the compound aspect of the present invention the above described process produces novel uracil and cytosine derivtives. Among such derivatives are compounds having the following general formulas

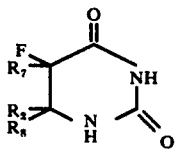

where $R_7$ is hydrogen, bromine, chlorine, fluorine or lower alkyl, $R_2$ is hydrogen or lower alkyl, and $R_8$ is lower alkoxy, including lower fluoroalkoxy, provided, however, that when $R_7$ and $R_2$ are both hydrogen, then $R_8$ is lower fluoroalkoxy; and

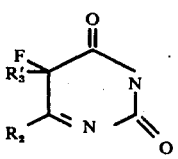

wherein $R'_3$ is bromine, chlorine, fluorine or lower alkyl and $R_2$ is hydrogen or lower alkyl. These novel compounds are useful as germicidal agents being active, for example, against gram negative and gram positive bacteria and against yeasts and fungi. This is in agreement with the use of other uracil derivatives disclosed in U.S. Pat. No. 3,277,092, the disclosure of which is hereby incorporated by reference.

As novel compounds of the present invention there may be mentioned:
5,5-difluorouracil
5-fluoro-5-methyluracil
5,5-difluoro-5,6-dihydro-6-(2,2,2-trifluoroethoxy) uracil as well as the novel intermediate products discussed above.

Broadly speaking, the novel uracil and cytosine derivatives produced by the present invention include compounds having the following general formulae:

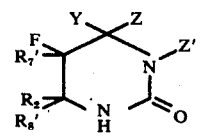

wherein $R_7'$ is hydrogen, bromine, chlorine, fluorine or lower alkyl, $R_2$ is hydrogen or lower alkyl, $R_8'$ is lower acyloxy, including lower haloacyloxy fluorine or lower alkoxy, including lower haloalkoxy, provided, however, that when $R_7'$ is hydrogen, bromine or chlorine, and $R_2$ is hydrogen, then $R_8'$ is fluorine or lower fluoroalkoxy, and Y, Z and Z' are defined hereinabove;

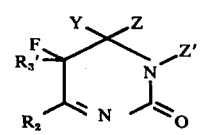

and wherein $R_3'$ is bromine, chlorine, fluorine or lower alkyl and $R_2$ is hydrogen or lower alkyl, and Y, Z and Z' have been defined hereinabove. These compounds have the same uses as described hereinabove.

The following examples are illustrative embodiments of the present invention. Unless otherwise expressed, all parts and percentages are by weight.

EXAMPLE 1

Preparation of 5,5-difluoro-5,6-dihydro-6-(2,2,2-trifluoroethoxy) uracil 5-fluorouracil (1.00 g, 0.0077 moles) was suspended in anhydrous 2,2,2-trifluoroethanol (20 ml) and treated with an equal volume mixture of gaseous fluorine and nitrogen at 68°-70° C for 103 minutes at which time gaseous fluorine was detected leaving the reaction vessel, representing a consumption of 0.0182 moles of fluorine. The mole ratio of fluorine to 5-fluorouracil was 2.36. The solvent was removed under reduced pressure at room temperature (25° C) to give a white solid which was dried at 50° C at reduced pressure. The product was identified as 5,5-difluoro-5,6-dihydro-6-(2,2,2-trifluoroethoxy) uracil (1.67g) representing a yield of 79.5% with a melting point of 142°-146° C; NMR confirmed the structure.

| Element | Theory (%) | Found (%) |
|---|---|---|
| C | 29.05 | 29.27 |
| H | 2.03 | 2.19 |
| N | 11.29 | 11.53 |

EXAMPLE 2

Preparation of 5,5-difluorouracil 5-fluorouracil (1.00 g) in anhydrous trifluoroacetic acid (20 ml) was reacted with a gaseous mixture of fluorine and nitrogen at 25° C until fluorine was detected leaving the reaction vessel. The crude reaction mixture was filtered to give a solid (0.03g) and the remaining solution evaporated to dryness in a vacuum oven at 60° C. The resulting residue was a white solid which was extracted with ether and the extract evaporated to give 5,5-difluorouracil (1.00g). The 5,5-difluorouracil was subsequently recrystallized from a mixture of benzene, 1,4-dioxane and hexane, NMR analysis confirmed its structure.

EXAMPLE 3

Preparation of 5-fluoro-5-methyl uracil 5-methyluracil (1.00 g) in trifluoroacetic acid (10 ml) was treated with gaseous fluorine-nitrogen mixture. The reaction began at an initial temperature of 0° C and during the fluorination the reaction temperature was raised to 14° C and the reaction continued until completion for 120 minutes. The mole ratio of fluorine to 5-methyl-uracil was 2.56. The solvent was evaporated at about 50° C under reduced pressure leaving a brown solid, which upon extracting with acetone gave 5-fluoro-5-methyluracil (0.21g) whose structure was confirmed by NMR analysis.

EXAMPLE 4

Preparation of 5-fluoro-6-(2,2,2-trifluoroethyoxy)-5,6-dihydrouracil

Uracil (0.50g, 0.00446 moles) was suspended in anhydrous 2,2,2-trifluoroethanol (20 ml) and treated with an equal volume mixture of fluorine and nitrogen at 55°-60° C. At the end of 74 minutes the reaction mixture was a clear solution and the introduction of fluorine and nitrogen was stopped; the total fluorine passed was about 0.0136 moles. The product was cooled in ice water and a white crystalline solid precipitated which was collected, dried at 50° C under reduced pressure and identified as 5-fluoro-6-(2,2,2-trifluoroethoxy)-5,6-dihydrouracil (0.67g), representing a yield of 65.3%. The elemental analysis indicated the following:

| Element | Theoretical (%) | Found (%) |
|---|---|---|
| C | 31.32 | 31.09 |
| H | 2.63 | 2.53 |
| N | 12.17 | 12.03 |
| F | 33.02 | 32.81 | and NMR analysis confirmed the structure to be:

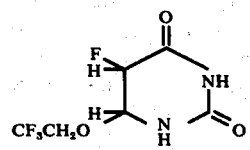

A portion of the 5-fluoro-6-(2,2,2-trifluoroethoxy)-5,6-dihydrouracil (0.12g) was heated with a hot air gun to 220° C. The slightly charred product was 5-fluorouracil (0.07g) as confirmed by infrared analysis.

EXAMPLE 5 – 7 and Comparative Examples A and B

In accordance with the procedure used in Example 1, uracil and derivatives thereof were reacted with the selected solvent at the stated temperature to produce the products of the following tables. Also included, for the sake of completeness, is essential data taken from Examples 1–4.

TABLE A

| EXAMPLE | REACTANT | | SOLVENT | TEMPERATURE (° C) | PRODUCT | | | YIELD (%) |
|---|---|---|---|---|---|---|---|---|
| | $R_1$ | $R_2$ | | | $R_3$ | $R_4$ | $R_5$ | |
| 1 | F | H | $CF_3CH_2OH$ | 68–70 | F | H | $CF_3CH_2O$ | 80(a) |
| 4 | H | H | $CF_3CH_2OH$ | 55–60 | H | H | $CF_3CH_2O$ | 65(b) |

(a) by evaporation of solvent
(b) by precipitation at 0° C

TABLE B

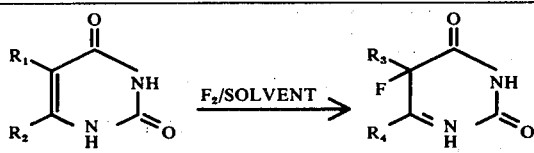

| EXAMPLE | REACTANT | | SOLVENT | TEMPERATURE (° C) | PRODUCT | | YIELD (%) |
|---|---|---|---|---|---|---|---|
| | $R_1$ | $R_2$ | | | $R_3$ | $R_4$ | |
| 2 | F | H | CF$_3$COOH | 20–25 | F | H | 85 |
| 3 | CH$_3$ | H | CF$_3$COOH | 14 | CH$_3$ | H | 30 |
| 5 | H | H | CF$_3$COOH | 51–58 | F | H | high |
| 6 | H | H | CCl$_3$COOH | 60 | F | H | 85 |

TABLE C

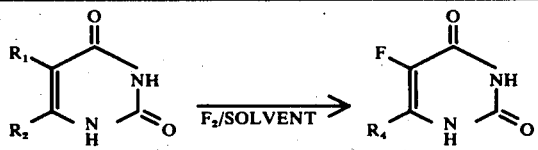

| EXAMPLE | REACTANT | | SOLVENT | TEMPERATURE (° C) | PRODUCT | YIELD (%) |
|---|---|---|---|---|---|---|
| | $R_1$ | $R_2$ | | | $R_4$ | |
| 7 | H | H | CF$_3$COOH | 20–25 | H | 64 |
| A* | H | H | CH$_3$COOH | 20 | H | 52 |
| B* | H | H | HF(Anhyd) | 0–5 | H | 6 |

*According to Belgian Patent 748,468.

Comparative Examples A and B are according to the disclosure of Belgian Pat. No. 748,468 to Knunyants, German and Kazmina. As will be appreciated when anhydrous hydrofluoric acid is the reaction solvent (Comparative Example B) the yield is low. The reactions required several hours in order to go to completion, 12 to 15 and 7 hours for Comparative Examples A and B, respectively, in contrast to the relatively short reaction times according to the present invention.

EXAMPLE 8

Preparation of 5,6-difluoro-5,6-dihydrouracil and 5-fluoro-6-trifluoroacetoxy-5,6-dihydrouracil.

49.0 g of uracil (0.437 moles) dissolved in 200 ml of anhydrous trifluoroacetic acid (2.43 moles) was reacted with about 3900 ml/hour of a gaseous 1:1 volume mixture of fluorine and nitrogen at 0° C. in a Teflon system, with care taken to avoid the presence of water in the reaction system. The reaction was discontinued when fluorine was detected leaving the reaction vessel, and the trifluoroacetic acid solvent was evaporated at a temperature of about 25° C. under a vacuum of < 1 mmHg, leaving a dry white solid which was a mixture of 5,6-difluoro-5,6-dihydrouracil and 5-fluoro-6-trifluoroacetoxy-5,6-dihydrouracil.

EXAMPLE 9

Preparation of 5-fluorocytosine 1.0g of cytosine (0.01 mole) was dissolved in 9cc of trifluoroacetic acid, probably with the formation of the cytosine acid salt. The solution was placed in a large test tube at a temperature of −5° C. and fluorinated with a mixture of elemental fluorine and nitrogen, with the gas flow rates being 13 cc/min. of fluorine and 13 cc/min. of nitrogen. The reaction temperatures were controlled within the range of from −5° C. to 0° C. After 0.014 moles of fluorine were added to the reaction system, the system was flushed with pure nitrogen and the trifluoroacetic acid solvent was evaporated off at 80° C. under a vacuum of < 1 mmHg, leaving a viscous liquid. A white solid precipitated from the viscous liquid upon standing, and a similar white solid was obtained from the freshly prepared viscous liquid by precipitation with acetone, with no appreciable difference between the two white solids so obtained as indicated by infrared spectrum comparison. NMR analysis (DMSO solution) indicated that the white solid was 5-fluorocytosine trifluoroacetic acid salt and ⅔ cytosine trifluoroacetic acid salt. Neutralization of the white solid reaction mixture (dissolved in water) with dilute sodium hydroxide yielded a mixture of 5-fluorocytosine and cytosine.

As indicated above, the conditions under which the fluorination reaction will take place are quite varied. We consider our invention inclusive of all operable conditions under which fluorine will react with uracil, cytosine and derivatives thereof. However, it may be said that we prefer to react the fluorine with at least 0.01% uracil, or other pyrimidine compound although much more concentrated solutions and slurries of uracil or other pyrimidine compound may be used; so far as we are aware, there is no upper limit to the concentration of dispersed uracil or other pyrimidine but if a high-solids slurry is used, care should be taken to see that all of the uracil or other pyrimidine compound is moistened with the solvent. Preferably, at least 10% of the solvent, based on the weight of mixture (or a mixture of at most 90% uracil or other pyrimidine compound and at least 10% solvent), should be present.

The fluorine may be diluted with any practical amount of inert gas; we have found that a mixture by volume of nine parts nitrogen to one part fluorine is more than enough to insure against the possibility of explosions. Any ratio by volume of nitrogen or other inert gas to fluorine from 9:1 to 1:3 may be conveniently used. A volume ratio of nitrogen to fluorine of from 1:1 to 3:1 is preferred. The fluorine need not be diluted at all, but the rate of introduction of fluorine to the reaction zone should be controlled to minimize the possibility of explosion if undiluted fluorine is used. This may be accomplished simply by observing the rate of reaction.

The reaction may be performed in batches or continuously.

Based on the preceding examples it will be apparent that other uracil and cytosine derivatives may be prepared by substituting the appropriate material for the starting compound.

Although aryl group-substituted pyrimidine derivatives have not been discussed in the foregoing detailed description, it is believed possible to obtain uracil derivative starting materials with aryl groups and substituted aryl groups in the 1,3,5 and 6 positions, and cytosine derivatives with aryl groups and substituted aryl groups in the 1,4,5 and 6 positions, which should produce the corresponding fluorinated aryl-substituted uracil and cytosine derivatives. Representative aryl groups are phenyl and ortho-, meta- and para-substituted phenyl groups having substituents such as $NO_2$, $SO_3H$, $SO_3H$, $SO_3NA$, $NH_2$, OH, halogen and the like. The non-aqueous fluorination process according to the novel process of this invention, and the corresponding fluorinated products produced thereby, have not been described owing to the commercial unavailability of these aryl-substituted compounds at this time. Similarly, starting materials having the 1 and/or 3 nitrogens substituted with alkyl groups have not been described but should also undergo fluorination when used as the starting material as described in this invention.

In addition to the above nitrogen-substituted pyrimidine compounds, it appears likely, from results obtained hereinabove, that cytosine derivatives having substituents, such as alkyl radicals and the like, on the nitrogen atom attached to the 4-carbon atom should also be appreciated starting materials for the process of the present invention.

2-Thiouracil and 2-carboxymethylthiouracil are known compounds. The results obtained with uracil suggest that these compounds, and other uracil derivatives wherein the oxygen atom on the 2-position carbon atom has been replaced by a sulfur atom or a substituted thio group, would also be suitable starting materials for the process of the present invention, to produce the corresponding 5-fluoro-2-thio- or 2-substituted thio-uracil compounds.

In addition to the above, it should be possible to prepare the arabinoside of 5-fluorocytosine and 5-fluorouracil by fluorinating the corresponding unfluorinated arabinosides of these compounds, as well as other N-glycosides of uracil and cytosine.

From the above, it will be appreciated that the results obtained to date suggest that compounds broadly of the general formula

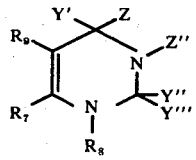

wherein $R_9$ is hydrogen, fluorine, chlorine, bromine, lower alkyl, aryl, alkaryl or aralkyl, $R_7$ is hydrogen, lower alkyl, aryl, alkaryl or aralkyl, $R_8$ is hydrogen, lower alkyl, aryl, alkaryl or aralkyl, or a glucoside radical, Y' is

and Z and Z'' together are a 3,4-double bond, or else Y' and Z, taken with the 4-carbon atoms, is carbonyl and Z'' is hydrogen, alkyl, aryl, alkaryl, or aralkyl, wherein $R_{11}$ and $R_{12}$ are independently hydrogen, alkyl, aryl, alkaryl or aralkyl, Y'' and Y''', taken together are =O =S, or else Y'' is hydrogen and Y''' is $—S—(CH_2)_{n''}—COOH$, wherein $n''$ is a value from 1 – 4 (The term "lower alkyl" refers to alkyl groups which can be straight or branched chains, having 1 – 6 carbon atoms. The aryl, alkaryl and aralkyl groups mentioned above contain from 6 – 14 carbon atoms, such as phenyl, benzyl, naphthyl, tolyl, phenethyl, xylyl, and the like), can be fluorinated with gaseous fluorine in the solvents described hereinabove to produce the corresponding 5-fluoro-uracil compounds broadly having the general formula

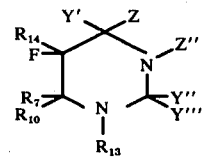

wherein $R_{14}$ is $R_9$ or, taken with $R_{10}$, 5,6-double bond, $R_{10}$ is lower alkoxy, lower fluoroalkoxy, a 5,6-double bond when taken with $R_{14}$, or a 1,6-double bond when taken with $R_{13}$, $R_{13}$ is $R_8$, or taken with $R_{10}$, 1,6-double bond.

It is further believed that the reaction conditions described hereinabove, for producing e.g., 5-fluorouracil would be applicable for this broader class of pyrimidine derivative fluorinations.

Uses for 5-fluoropyrimidine derivatives, as described above, are described in Japanese Pat. Nos. 12774/67; 12777/67; 4,428/69; 32,078/69; 17,911/69; 24,419/68; 21,029/71; 12,387/60; 9577/61; 7,947/68, the disclosures of which are hereby incorporated by reference.

It will be appreciated that the starting materials used in the present application may be conveniently prepared by reacting the appropriate uracil or derivative thereof in an acid and/or alcohol reaction solvents according to the teachings herein. These starting materials are also prepared from the corresponding uracil materials in aqueous solutions as disclosed in copending application of Schuman et al, Ser. No. 186,444, filed Oct. 4, 1971, U.S. Pat. No. 3,954,758, entitled "5-Fluorouracil Derivatives and Process for Producing 5-Fluorouracil and Derivatives Thereof in Aqueous Solvents", the disclosure of which is hereby incorporated by reference.

What is claimed is:

1. A process for the fluorination of pyrimidines, said process consisting essentially of reacting, in a solvent of the formula:

$$CX''_2Y''—(CY''_2)_n—COOH$$

or $$CX_2Y—(CY_2)_n—CH_2OH,$$

wherein X and Y are independently hydrogen, bromine, chlorine or fluorine, X'' and Y'' are independently bromine, chlorine, or fluorine, and $n$ is an integer from 0 to 6, at a temperature of about the solvent freezing point to about the solvent boiling point, a pyrimidine of the formula

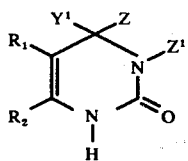

with at least about a stoichiometric amount of gaseous fluorine to produce a compound of the formula:

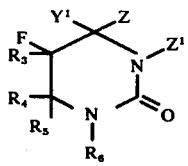

wherein $R_1$ is hydrogen, fluorine, chlorine, bromine or lower alkyl, $R_2$ is hydrogen or lower alkyl, $R_3$ is $R_1$ or, taken with $R_5$, a 5,6-double bond, $R_4$ is hydrogen or lower alkyl, $R_5$ is
$CX_2Y-(CY_2)_n-CH_2O-$,
$CX''_2Y''-(CY''_2)_n-COO-$,
a 5,6-double bond when taken with $R_3$, or a 1,6-double bond when taken with $R_6$, $R_6$ is hydrogen or a 1,6-double bond when taken with $R_5$, $Y^1$ is $-NH_2$ and Z and $Z^1$ together are a 3,4-double bond or else $Y^1$ and Z taken with the 4-carbon atom, are carbonyl and $Z^1$ is hydrogen.

2. Process as claimed in claim 1 wherein said solvent is of the formula:
$CX''_2Y''-(CY''_2)_n-COOH-$.

3. Process as claimed in claim 2 wherein said solvent is trifluoroacetic acid.

4. Process as claimed in claim 1, wherein the reaction solvent has the formula:
$CX_2Y-(CY_2)_n-CH_2OH$.

5. Process as claimed in claim 4 wherein X and Y are halogen.

6. Process as claimed in claim 5 wherein said halogen is fluorine.

7. Process as claimed in claim 1, wherein Y is $-NH_2$ and Z and $Z'$ together are a 3,4-double bond.

8. Process as claimed in claim 1 wherein the molar ratio of fluorine to said pyrimidine is from about 1:1 to about 2:1.

9. Process as claimed in claim 1 wherein an effluent gas stream is discharged from the reaction zone and the reaction is continued at least until fluorine is detected in the effluent gas.

10. Process as claimed in claim 1, wherein X'' and Y'' are fluorine.

11. A process for the fluorination of uracil and derivatives thereof consisting essentially of reacting in a solvent at a temperature of about 0° C. to about the solvent boiling point, a uracil derivative of the formula:

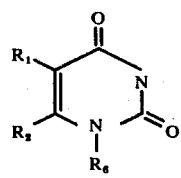

with at least about a stoichiometric amount of gaseous fluorine to prepare a compound of the formula:

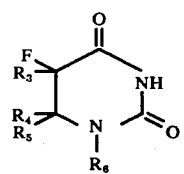

wherein
$R_1$ is a hydrogen, fluorine, chlorine, bromine or lower alkyl,
$R_2$ is hydrogen or lower alkyl,
$R_3$ is hydrogen, fluorine, chlorine, bromine, lower alkyl or taken with $R_5$ a 5,6-double bond,
$R_4$ is hydrogen or lower alkyl,
$R_5$ is a 5,6-double bond when taken with $R_3$ or a 1,6-double bond when taken with $R_6$ and
$R_6$ is hydrogen or a 1,6-double bond when taken with $R_5$,
the reaction conducted in a solvent which is $CX''_2Y''(CY''_2)_n-COOH$
wherein X'' and Y'' are independently bromine, chlorine or fluorine, and n is an integer from 0 to 6, and heating the resulting product to produce said compound.

12. The process of claim 11, wherein each X'' and Y'' is fluorine.

13. A process for the fluorination of uracil and derivatives thereof consisting essentially of reacting in a solvent at a temperature of about 0° C to about the solvent boiling point, a uracil derivative of the formula:

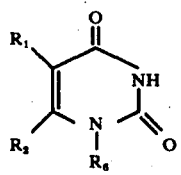

with at least about a stoichiometric amount of gaseous fluorine to prepare a compound of the formula:

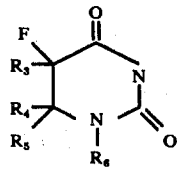

wherein
$R_1$ is hydrogen, fluorine, chlorine, bromine or lower alkyl,
$R_2$ is hydrogen or lower alkyl,
$R_3$ is hydrogen, fluorine, chlorine, bromine, or lower alkyl,
$R_4$ is hydrogen or lower alkyl,
$R_5$ is $CX_2Y(CY_2)_n-CH_2O-$, wherein X, Y and n are defined below,
$R_6$ is hydrogen,
the reaction conducted in a solvent which is $CX_2Y-(CY_2)_n-CH_2OH$ wherein X and Y are independently hydrogen, bromine, chlorine or fluorine, and *n* is an integer from 0 to 6.

14. The process of claim 13 wherein the reaction is conducted at a temperature of about 52° to about 75° C.

15. The process of claim 13 wherein the reaction solvent is trifluoroethanol.

16. The process of claim 11, wherein the molar ratio of fluorine to said uracil derivative is from about 1:1 to about 2:1.

17. The process of claim 11, wherein the reaction is continued at least until fluorine is detected in the effluent gas.

18. The process of claim 11, wherein the reaction solvent is selected from the group consisting of trifluoroacetic acid, and trichloroacetic acid.

19. A method for producing 5-fluorouracil comprising reacting uracil with fluorine in trifluoroacetic acid at a temperature from about 14° to about 58° C in an inert gas atmosphere.

20. The method of claim 19, wherein said inert gas is nitrogen.

21. The process of claim 13 wherein the molar ratio of fluorine to said uracil derivative is from about 1:1 to about 2:1.

22. The process of claim 13 wherein the reaction is continued at least until fluorine is detected in the effluent gas.

23. The process of claim 14, wherein X and Y are halogen.

24. The process of claim 23, wherein said halogen is fluorine.

* * * * *